United States Patent [19]

Kruger et al.

[11] Patent Number: 4,680,025
[45] Date of Patent: Jul. 14, 1987

[54] BLOOD COMPONENT COLLECTION SYSTEMS AND METHODS

[75] Inventors: Robert J. Kruger, Arlington Heights; Richard I. Brown, Northbrook, both of Ill.

[73] Assignee: Baxter Travenol Laboratories, Inc., Deerfield, Ill.

[21] Appl. No.: 833,530

[22] Filed: Nov. 27, 1984

Related U.S. Application Data

[63] Continuation of Ser. No. 411,058, Aug. 24, 1982, abandoned.

[51] Int. Cl.$^4$ ............................................. A61M 37/00
[52] U.S. Cl. ........................................ 604/6; 604/4
[58] Field of Search ...................................... 604/4–6, 604/408, 410–411, 414, 905, 262; 210/259, 927, 433.2; 494/36

[56] References Cited

U.S. PATENT DOCUMENTS

| | | | |
|---|---|---|---|
| 2,876,769 | 3/1959 | Cordova | 604/6 |
| 3,228,876 | 1/1966 | Mahon | 604/5 |
| 3,655,123 | 4/1972 | Judson et al. | 604/6 |
| 3,802,432 | 4/1974 | Djerassi . | |
| 3,870,042 | 3/1975 | Viguier | 604/410 |
| 3,945,380 | 3/1976 | Dabney et al. | 604/6 |
| 3,986,506 | 10/1976 | Garber et al. . | |
| 4,157,723 | 6/1979 | Granzow et al. . | |
| 4,185,629 | 1/1980 | Cullis et al. | 128/214 R |
| 4,187,979 | 2/1980 | Cullis et al. | 604/6 |
| 4,191,182 | 3/1980 | Popovich et al. . | |
| 4,215,688 | 8/1980 | Terman et al. | 604/5 |
| 4,222,379 | 9/1980 | Smith . | |
| 4,223,672 | 9/1980 | Terman et al. . | |
| 4,265,280 | 5/1981 | Ammann et al. . | |
| 4,267,269 | 5/1981 | Grode et al. | 604/6 |
| 4,280,497 | 7/1981 | Warner et al. | 604/6 |
| 4,286,597 | 9/1981 | Gajewski et al. | 604/408 |
| 4,325,417 | 4/1982 | Boggs et al. . | |
| 4,332,122 | 6/1982 | Williams | 604/408 |
| 4,340,097 | 6/1982 | Ammann et al. . | |
| 4,381,775 | 5/1983 | Nosé et al. | 604/6 |

Primary Examiner—C. Fred Rosenbaum
Assistant Examiner—Gene B. Kartchner
Attorney, Agent, or Firm—Paul C. Flattery; Daniel D. Ryan; Bradford R. L. Price

[57] ABSTRACT

A blood component collection system and method each utilizes centrifugation to first separate whole blood into red blood cells and platelet-rich plasma. Noncentrifugal separation is then utilized to further separate the platelet-rich plasma into platelet concentrate and plasma which is virtually free of platelets. The system and method are applicable for use in association with both batch and continuous flow procedures.

4 Claims, 11 Drawing Figures

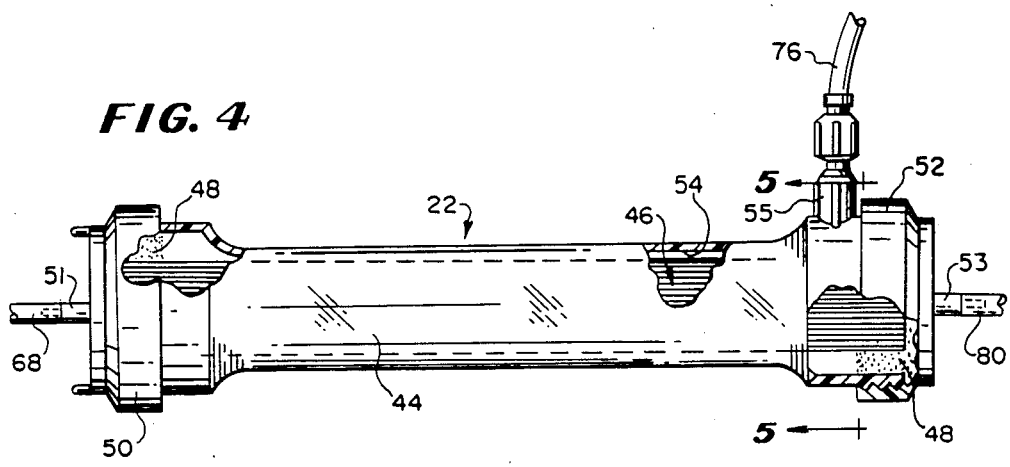
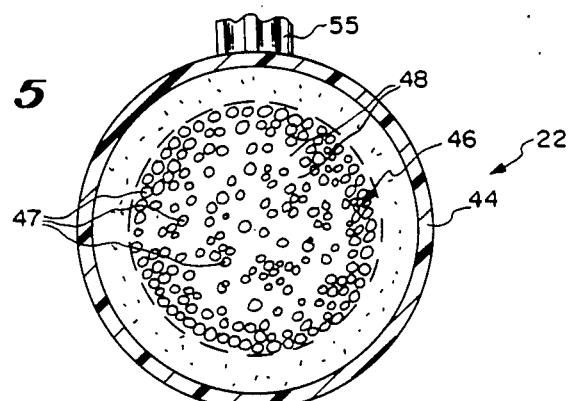
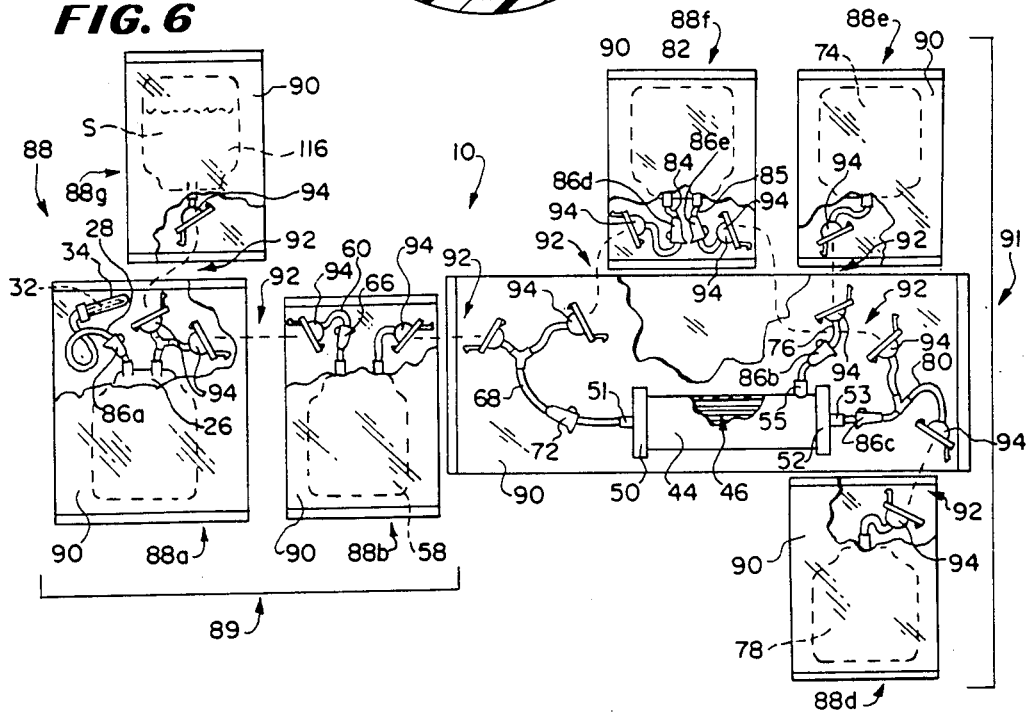

U.S. Patent  Jul. 14, 1987  Sheet 5 of 5  4,680,025
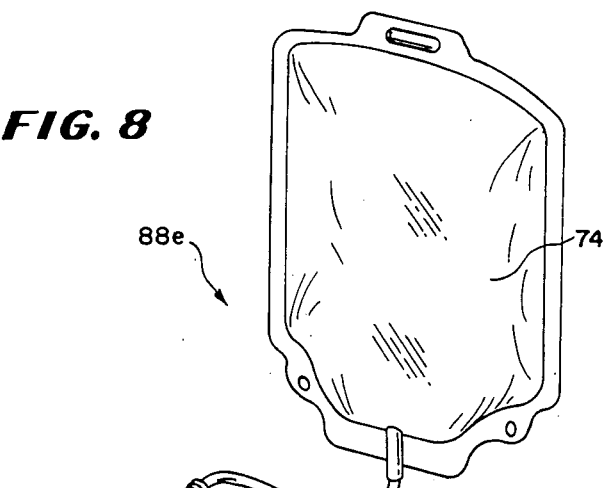
FIG. 8
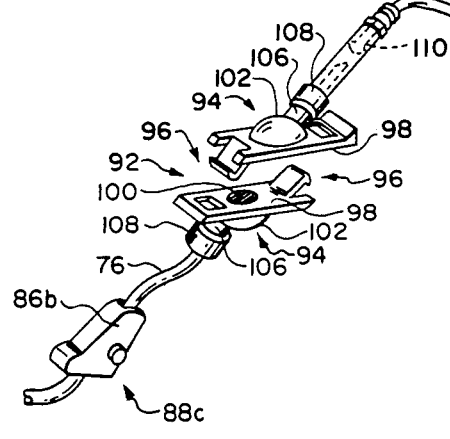
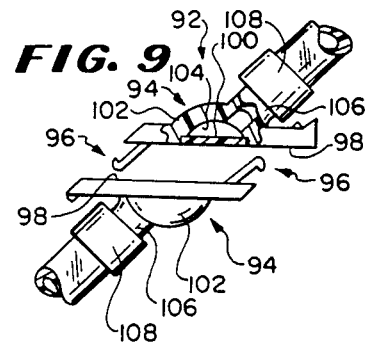
FIG. 9
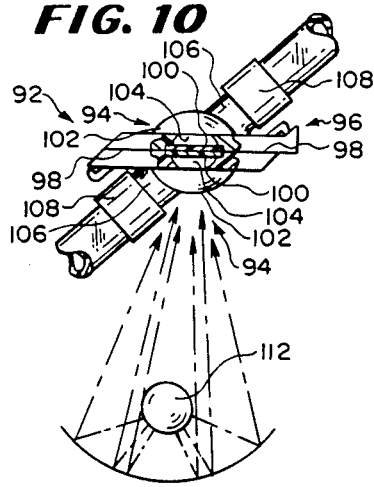
FIG. 10
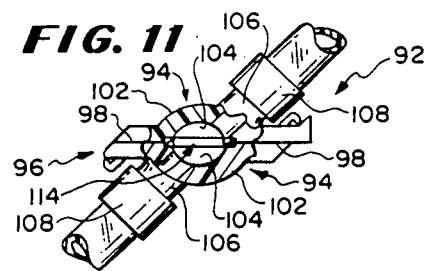
FIG. 11

BLOOD COMPONENT COLLECTION SYSTEMS AND METHODS

This is a continuation of application Ser. No. 411,058, filed Aug. 24, 1982 now abandoned.

FIELD OF THE INVENTION

This invention generally relates to systems and methods which enable the collection and separation of whole blood into its therapeutic components. This invention also generally relates to semipermeable membrane systems and methods.

BACKGROUND AND OBJECTS OF THE INVENTION:

At the present time, over 12 million units of whole blood are collected from volunteer donors in the United States each year. Because of the advent of blood component therapy, approximately 60% to 80% of the whole blood collected today is not itself stored and used for transfusion. Instead, the whole blood is first separated into its clinically proven components, which are themselves individually stored and used to treat a multiplicity of specific conditions and diseased states.

The clinically proven components of whole blood include red blood cells, which can be used to treat chronic anemia; platelet-poor plasma, from which Clotting Factor VIII-rich cryoprecipitate can be obtained for the treatment of hemophilia; and concentrations of platelets, which can be used to control thrombocytopenic bleeding.

The present medical consensus is that care of a patient is improved by providing only the therapeutic components of whole blood which are required to treat the specific disease. The demand for therapeutic components of whole blood is thus ever-increasing. Likewise, the demand for safe and effective systems and methods for collecting, separating, and storing the therapeutic components of whole blood grows accordingly.

One desirable feature for a blood collection and separation system and method is the capability to maximize, to the greatest extent possible, the yield of clinically proven blood components during a single collection procedure.

Minimum yield requirements for certain components are often prescribed by governmental regulations. For example, in the United States, Federal Regulations [Title 21 C.F.R. §640.24(c)] require the presence, per therapeutic unit of platelets, of at least $5.5 \times 10^{10}$ platelets in at least 75% of the units tested. Typically, a unit of platelets includes, as a suspension media, about 50 milliliters of plasma.

Another desirable feature for a blood collection and separation system and method is the capability of yielding components which are suited for storage for prolonged periods. This feature is closely related to the degree of sterility a given blood collection system can assure. Such matters are also usually the subject of governmental regulations.

For example, in the United States, whole blood and components which are collected and processed in a nonsterile, or "open", system must be transfused within twenty-four (24) hours of collection. On the other hand, in the United States, whole blood and red cells which are collected in a sterile, or "closed", system may be stored for upwards to thirty-five days, depending upon the type of anticoagulant and storage medium used. Likewise, platelets which are collected in a "closed" system may be stored for upwards to five days, and possibly longer, depending upon the ability of the storage container to maintain proper storage conditions. Plasma which is collected in a "closed" system may be frozen for even more prolonged storage periods.

In the United States, Federal Regulations [Title 21 C.F.R. §640.16(b)] define a "closed" blood collection system as one in which the initially sterile blood collection and transfer containers are integrally attached to each other and not open to communication with the atmosphere. Furthermore, to remain a "closed" blood collection system in the United States, the blood collection container of the system cannot be "entered" in a non-sterile fashion after blood collection. An entry into a blood collection system which presents the probability of non-sterility which exceeds one in a million (i.e., greater than $10^{-6}$) is generally considered in the United States to constitute a "non-sterile" entry.

Representative examples of known whole blood collection assemblies include the following U.S. Patents:

| | |
|---|---|
| Earl | 3,064,647 |
| Wandell et al | 3,078,847 |
| Bellamy Jr. | 3,110,308 |
| Tenczar Jr. | 3,187,750 |
| Viguier | 3,870,042 |
| Garber et al | 3,986,506 |
| Djerassi | 4,111,199 |
| Smith | 4,222,379 |

Representative examples of known commercially available whole blood collection assemblies are sold by Fenwal Laboratories, Inc. (a division of Travenol Laboratories, Inc., Deerfield, Ill.); Delmed Corp., Irvine, Calif.; and Cutter Laboratories, Inc., Berkeley, Calif.

All of the above-identified blood collection assemblies rely exclusively upon nonautomated batch centrifugation procedures to separate the collected unit of whole blood (approximately 450 milliliters) into its various components.

During conventional batch centrifugation, the collected unit of whole blood is first subjected to a centrifugal force for a period of time sufficient to initially separate the whole blood into red blood cells and plasma in which substantial amounts of platelets are present (known as platelet-rich plasma). This step of the procedure is commonly referred to as the "soft spin".

The platelet-rich plasma is then manually expressed into another container and subjected to a greater centrifugal force for generally a longer period of time to further separate the platelet-rich plasma into platelet concentrate and platelet-poor plasma. This step of the procedure is commonly referred to as the "hard spin".

During the course of nonautomated batch centrifugation, approximately 100 milliliters of plasma otherwise suited for storage or further fractionation is "lost", because some of it remains with the red blood cells after the soft spin, and some of it is transferred along with the platelets after the hard spin. Therefore, using conventional batch centrifugation, plasma yields cannot be optimized.

Furthermore, as the authors observe in S. J. Slichter et al, "Preparation and Storage of Platelet Concentrates (Factors Influencing the Harvest of Viable Platelets from Whole Blood)", *British Journal of Haematology*, 1976, 34, 395–402, "accurate, standardized centrifugation procedures are critical for efficient preparation of platelet concentrates". To harvest 86% of the platelets from a unit of whole blood without loss of viability, the authors recommend (on page 401 of the article) a soft spin of 1000 g (i.e., one thousand times the force of gravity) for 9 minutes, followed by a hard spin of 3000 g for 20 minutes.

Centrifugal procedures which optimize platelet yields thus tend to be time consuming. Furthermore, because skilled technicians are required to calibrate and operate the centrifuges used during these procedures, nonautomated batch centrifugation also tends to be labor intensive.

Additionally, because platelets will lose viability if spun too hard and/or too long, it is extremely difficult, if not impossible, to create centrifugal forces during a conventional hard spin sufficient to separate virtually all of the platelets from the plasma. For example, the Slichter et al article observes (on page 397) that platelet-poor plasma obtained during conventional batch centrifugation techniques includes platelets present in a concentration of between 13,000 and 16,000 platelets per microliter.

The inability of conventional batch centrifugation techniques to yield virtually platelet-free plasma leads to further inefficiencies in blood component processing. For example, it has been observed that the presence of platelets in the plasma from which Clotting Factor VIII-rich cryoprecipitate is obtained reduces the effective yields of the Factor VIII. Thus, platelet-poor plasma obtained by conventional batch centrifugation techniques does not maximize, to the greatest extent possible, the yield of Factor VIII.

Furthermore, the measurable presence of platelets in platelet-poor plasma means, of course, that these platelets are not present in the platelet concentrate. Thus, conventional batch centrifugation techniques do not maximize, to the greatest extent possible, the yield of platelet concentrate.

Therefore, another desirable feature of blood collection and separation systems and methods is the ability to obtain optimal yields of platelets and virtually platelet-free plasma.

A novel blood collection system which is capable of optimizing component yields using exclusively nonautomated batch centrifugation techniques is disclosed in copending Ronald A. Williams et al, U.S. patent application No. 373,555, filed Apr. 30, 1982, and entitled INCREASED YIELD BLOOD COLLECTION SYSTEMS AND METHODS, now abandoned which is a continuation-in-part of U.S. patent application No. 316,918, filed Oct. 30, 1981, now abandoned.

A novel blood collection system which is capable of optimizing component yields and attendant storage times using a "continuous flow" centrifugation technique is disclosed in Ronald A. Williams et al, patent application No. 403,832 (filed July 30, 1982) and entitled INCREASED YIELD CONTINUOUS FLOW BLOOD COMPONENT COLLECTION SYSTEM now abandoned.

Novel blood collection systems and methods which utilize a microporous membrane to perform all or part of an extended yield blood collection procedure are disclosed in Bloom et al U.S. patent application Ser. No. 766,664, filed Aug. 15, 1985, entitled "Increased Yield Blood Component Collection Systems and Methods" now abandoned, which is a continuation of U.S. patent application Ser. No. 641,345, filed Aug. 15, 1984 now abandoned, which is a continuation of U.S. patent application Ser. No. 411,056, filed Aug. 24, 1982, now abandoned; as well as in Bilstad et al. U.S. patent application Ser. No. 690,399, filed Jan. 9, 1985, entitled "Increased Yield Blood Component Collection Systems and Methods", which is a continuation of U.S. patent application Ser. No. 411,057, filed Aug. 24, 1982 now abandoned. The parent applications of these two cases share the same earliest filing date as the now abandoned parent of the instant application.

With the foregoing considerations in mind, one of the principal objects of this invention is to provide blood collection systems and methods which maximize, to the greatest extent possible, the yield of blood components obtained during a single collection procedure in a manner which also assures the maximum available storage period for each of the components collected, as measured by applicable United States standards.

Another principal object of this invention is to provide blood collection systems and methods which, in addition to the above-described attributes, provides plasma which is virtually platelet-free.

Yet another principal object of this invention is to provide blood collection systems and methods which, in addition to any of the above-described attributes, minimizes, to the greatest extent possible, the overall time involved during a given procedure.

Yet another one of the principal objects of this invention is to provide blood collection systems and methods which, in addition to the just described attributes, need not depend entirely upon costly, relatively large, and sophisticated processing devices.

SUMMARY OF THE INVENTION

To achieve these and other objects, the invention provides a blood component collection system which comprises first means for collecting whole blood from a donor for separation into essentially red blood cells and platelet-rich plasma. The system also includes second means for receiving the platelet-rich plasma from the first means and for noncentrifugally separating the platelet-rich plasma into platelet concentrate and virtually platelet-free plasma.

As used herein, the term "platelet-rich plasma" means that platelets are present in a concentration of about twice that normally found in the whole blood of the donor. Generally, the normal concentration of platelets in a healthy adult is about 200,000 platelets per microliter of whole blood. Thus, the associated platelet-rich plasma from this donor would have a platelet concentration of approximately 400,000 platelets per microliter of plasma.

As used herein, plasma is "virtually platelet-free" when the platelet concentration is about 12,000 platelets per microliter of plasma or less. The infusion of platelets in these small concentrations is generally recognized by the medical community to exert no significant therapeutic effect upon the human body, when compared to the therapeutic effect of infusions of platelets in larger concentrations. Thus, the therapeutic value of plasma which is virtually platelet-free is attributable solely to the plasma and plasma-based components other than platelets. Plasma which is virtually platelet-free can itself be infused for therapeutic purposes, or it can be used as source plasma for fractionation purposes.

As used herein, platelets are in "concentrated" form when they are present in a concentration which meets or exceeds the prevailing minimum platelet yield requirements prescribed by governing regulations.

In a preferred embodiment, the second means includes means for collecting volumes of the platelet concentrate and the virtually platelet-free plasma for storage. In this arrangement, the first means also includes means for collecting a volume of the red blood cells for storage.

In a preferred embodiment, each of the blood component collecting means includes means for imparting a physical characteristic which is beneficial to the intended function of the associated collecting means. For example, the physical characteristic imparted to the collecting means for the platelet concentrate includes improved gas transmission characteristics for improved platelet survival; the physical characteristic imparted to the collecting means for the virtually platelet-free plasma includes relatively high low-temperature strength to facilitate freezing of the virtually platelet-free plasma; and the physical characteristic imparted to the collecting means for the red blood cells is the suppression of hemolysis in red blood cells during storage.

In a preferred embodiment, the first means includes container means operative for placement within the centrifugal separation chamber of an extracorporeal blood processing device to undergo centrifugation. In this arrangement, the second means preferably includes microporous membrane means operative for filtering the cellular components from the noncellular components of blood. Because the filtration of platelets (a cellular component) from plasma (a noncellular component) can occur virtually instantaneously, significant savings in time can be achieved, compared to the time involved in centrifugally separating these components.

The system which embodies the features of the invention is applicable for use in the context of either a nonautomated batch centrifugation process or a continuous flow procedure.

In the continuous flow embodiment, the first means further includes means for returning the red blood cells to the donor. The first means can also include means for diverting a volume of the red blood cells away from the donor for storage. Preferably, the red blood cell diversion means includes the physical characteristic of suppressing hemolysis in red blood cells during storage.

In the most preferred embodiment, the system comprises a "closed" system, as measured by applicable regulations. Components which are collected in the system can thus be stored for the maximum permissible times.

The invention also provides a blood component collection method which comprises the steps of centrifugally separating a volume of whole blood essentially into red blood cells and platelet-rich plasma, and subsequently noncentrifugally separating the platelet-rich plasma into platelet concentrate and virtually platelet-free plasma. Preferably, each of the steps is done in a manner which does not expose the whole blood and its components to communication with the atmosphere.

The system and method which embody the features of the invention each provides virtually platelet-free plasma, thereby maximizing platelet yields, in a manner which involves significantly less time and manual labor than conventional centrifugation processes.

Other features and advantages of the invention will be pointed out in, or will be apparent from, the specification and claims, as will obvious modification of the embodiment shown in the drawings.

DESCRIPTION OF THE DRAWINGS

FIG. 4 is an enlarged side view, with portions broken away and in section, of the microporous membrane means which is associated with the systems shown in both FIG. 2 and 3;

FIG. 5 is a end section view, with a portion broken away and in section, of the microporous membrane means taken generally along line 5—5 in FIG. 4;

FIG. 6 is a plan view, with portions broken away and in section, of an increased yield blood component collection assembly which embodies the features of the system shown in FIG. 2;

FIG. 8 is an enlarged view of a portion of the assembly shown in FIG. 6;

FIG. 9 is a further enlarged view, with portions broken away and in section, of a portion of the assembly shown in FIG. 6, showing the connector means associated with the assembly in an uncoupled relationship;

FIG. 10 is an enlarged view, with portions broken away and in section, of the connector means shown in FIG. 9 in a coupled relationship and being exposed to a radiant energy-induced melting apparatus to open a fluid path therethrough; and FIG. 11 is an enlarged view, with portions broken away and in section, of the connector means shown in FIG. 10 after the fluid path has been opened therethrough.

Before explaining the embodiments of the invention in detail, it is to be understood that the invention is not limited in this application to the details of construction and the arrangement of components as set forth in the following description or as illustrated in the accompanying drawings. The invention is capable of other embodiments and of being practiced or carried out in various ways. Furthermore, it is to be understood that the phraseology and terminology employed herein is for the purpose of description and should not be regarded as limiting.

DESCRIPTION OF THE PREFERRED EMBODIMENTS

Figure 1:
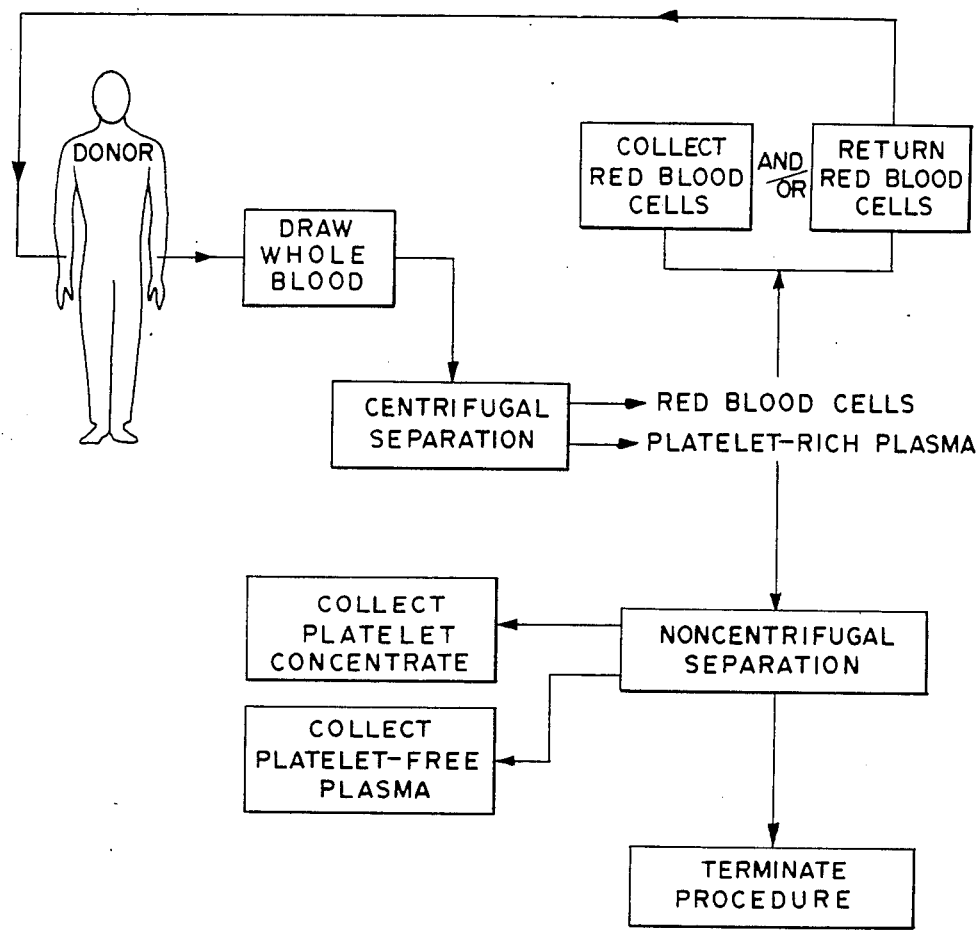
FIG. 1 is a functional block diagrammatic view of an increased yield blood component collection method which embodies the features of the invention.

A blood component collection method which embodies the features of the invention is shown in FIG. 1. The method includes the step of separating a volume of whole blood essentially into red blood cells and platelet-rich plasma. The method next includes the step of separating the platelet-rich plasma into platelets and virtually platelet-free plasma.

The method preferably includes the additional steps of collecting the red blood cells, the platelet concentrate and the virtually platelet-free plasma, each for storage or further fractionation.

The method which embodies the features of the invention preferably utilizes the "soft spin" of a conventional nonautomated batch centrifugation technique to initially separate the whole blood into red blood cells and platelet-rich plasma. However, other comparable techniques may be utilized to achieve this initial separation.

The method which embodies the features of the invention also preferably utilizes, in combination with a centrifugal soft spin, the subsequent step of noncentrifugally separating the platelet-rich plasma into the platelet concentrate and virtually platelet-poor plasma.

Examples of "noncentrifugal" separation techniques include membrane filtration, glass fiber filtration, and depth filtration, as well as the use of absorption columns, chemical separation, electrical separation, and electromagnetic separation. Of these filtration and, in particular, membrane filtration is the preferred technique.

The method can also include the step of returning the red blood cells to the donor to achieve a continuous flow arrangement. In this operative environment, the method can optionally include the additional step of diverting a volume of the red blood cells away from the donor for storage purposes.

Preferably, each step of the method is done in a manner which does not expose the blood components to communication with the atmosphere. Maximum permissible storage time for each of the components collected is thereby achieved.

The significant features and advantages of the just-described method will become even more apparent after the following detailed description of increased yield blood component collection systems which embody the features of the invention.

Figure 2:
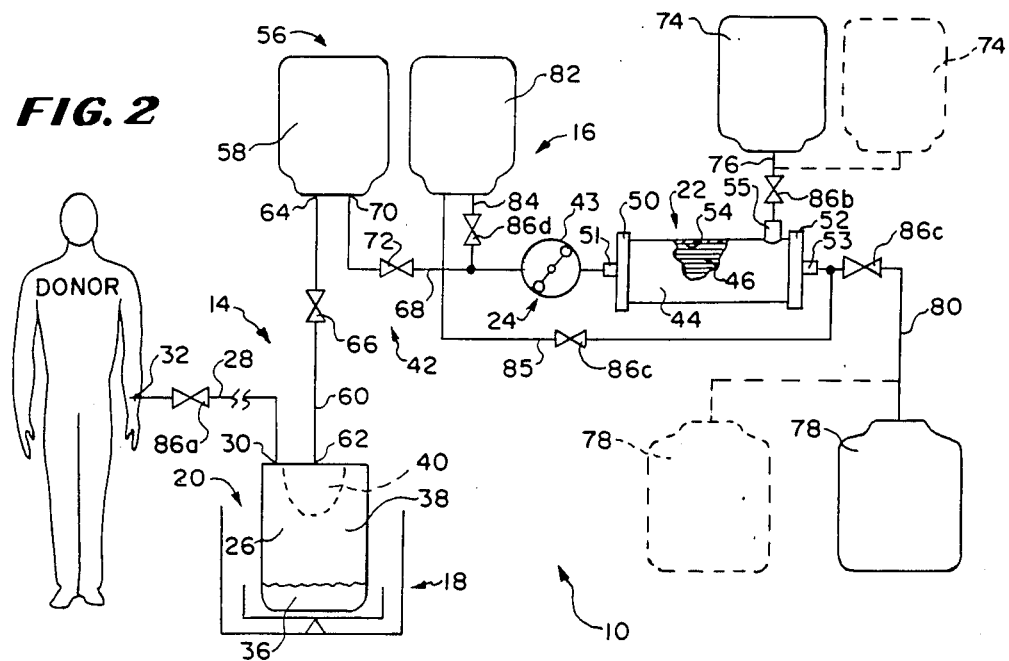
FIG. 2 is a functional diagrammatic view of an increased yield blood component collection system which embodies the features of the invention and which can carry out the method shown in FIG. 1.
Figure 3:
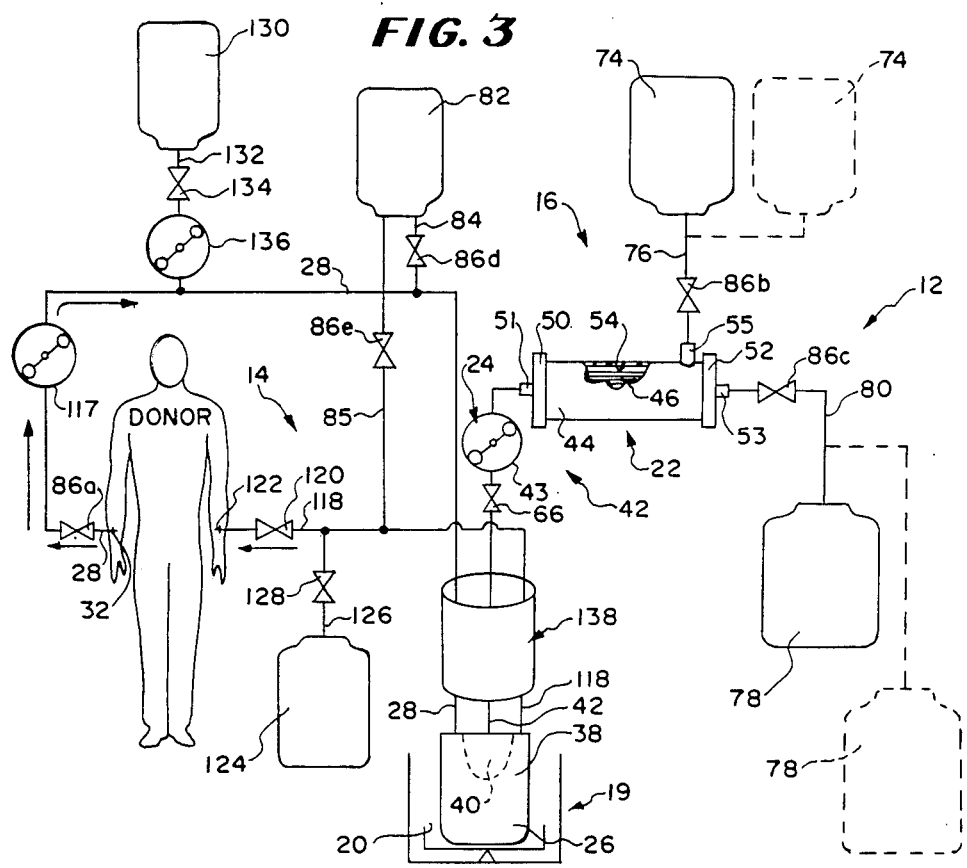
FIG. 3 is a functional diagrammatic view of another increased yield blood component collection system which embodies the features of the invention and which can carry out the method shown in FIG. 1.

Reference is now made to FIGS. 2 and 3. There, blood component collection systems, respectively 10 and 12, are shown. Each of the systems 10 and 12 embodies the features of the invention and can be used to carry out the method shown in FIG. 1. The system 10 shown in FIG. 2 is best suited for use in association with a nonautomated batch centrifugation process. The system 12 shown in FIG. 3 is best suited for use in association with a continuous flow centrifugation process.

Attention is first directed to the system 10 shown in FIG. 2.

As shown in FIG. 2, the system 10 comprises first means 14 or portion for collecting an aliquot, or unit, of whole blood from a donor for separation into essentially red blood cells and platelet-rich plasma. Typically, the aliquot can contain about 450 milliliters of whole blood.

The system 10 further includes second means 16 or portion for receiving the platelet-rich plasma from the first means 14 and for noncentrifugally separating the platelet-rich plasma into platelet concentrate and virtually platelet-free plasma.

The first and second means 14 and 16 may be variously constructed. However, in the illustrated embodiment (which corresponds with the preferred embodiment of the heretofore described method), the first means 14 is operative for use with an extracorporeal batch blood processing device 18 having a centrifugal separation chamber 20, both of which are shown schematically in FIG. 2. The second means 16 employs filtration to effect further separation of the platelet-rich plasma and includes microporous membrane means 22 which is operative for attachment to external pump means 24. More particularly, the microporous membrane means 22 of the second means 16 is operative for filtering the cellular components of blood (such as the platelets) from the non-cellular components (such as plasma).

In this preferred arrangement, the first means 14 includes a centrifugation container 26 which is suited for placement within the separation chamber 20 of the device 18 to undergo centrifugation.

The first means 14 further includes first branch conduit means 28 which communicates, at one end, with an inlet port 30 in the centrifugation container 26. The first branch means 28 communicates, at its other end, with a phlebotomy needle 32. Whole blood is introduced from the donor into the centrifugation container 26 through the first branch means 28.

The phlebotomy needle 32 may be intregally connected with the branch conduit means 28 and be normally sealed from communication with the atmosphere by conventional needle cover 34 or sheath (not shown in FIG. 2, but shown in FIG. 6). The cover 34 is removed at the time of venipuncture.

Alternately, the branch conduit means 28 can include a conventional needle adaptor (not shown), such as those provided in Fenwal Blood Recipient Sets, sold by Fenwal Laboratories, Inc., a division of Travenol Laboratories, Inc., Deerfield, Ill. The needle adaptor receives the needle 32 at the time of venipuncture.

To prevent the whole blood introduced into the container 26 from clotting, a volume of a conventional anticoagulant solution 36 (such as ACD or CPD) is carried in the container 26.

The whole blood which is introduced into the container 26 is subjected to a centrifugal force field developed within the chamber 20. Because of known differences in densities, components of the whole blood separate and congregate within the container 20 in different zones radially spaced from the rotational axis of the chamber 20.

The desired separation of the components depends upon the magnitude of the centrifugal forces developed. By using a Sorvall RC-3 centrifuge (HG-4L rotor) at 1900 RPM (1000xg), the whole blood can be separated in approximately 6 minutes into essentially red blood cells (which congregate in the zone 38 of the container 26) and platelet-rich plasma (which congregates in the zone 40 of the container 26).

The second means 16 of the preferred arrangement includes second branch means 42 which delivers the platelet-rich plasma from the zone 40 of the centrifugation container 26 to the microporous membrane means 22. The second branch means 42 includes a portion 43 which is operative for attachment to the pump means 24 for introducing the the platelet-rich plasma into the microporous membrane means 22.

In this arrangement, the red blood cells are preferably retained in the centrifugation container 26 for storage.

The microporous membrane means 22 may be variously constructed. In the illustrated embodiment, and as best shown in FIGS. 4 and 5, the membrane means 22 includes a tubular housing 44 in which a bundle of microporous hollow fiber membranes 46 is mounted. The membranes 46 can be mounted within the housing 44 utilizing conventional potting techniques, such as the one disclosed in Mahon, U.S. Pat. No. 3,228,876.

During the potting operation disclosed in the above patent, a liquid potting compound 48 (for example, polyurethane) is introduced into opposite ends of the housing 44 to impregnate the exterior areas of the membranes 46 about and between the ends 47 of the individual fibers (see FIG. 5). Ingress of the potting compound 48 into the bores of the fiber ends 47 can be prevented by various means, such as those discussed in the above-cited Mahon patent.

After the potting compound 48 has cured and the fiber ends 47 opened, end caps 50 and 52 may be sealed to the potted ends of the housing 44. An inlet port 51 is formed on the end cap 50, and an outlet port 53 is formed on the end cap 52.

Circumferentially surrounding the bundle of hollow fiber membranes 46 is an open volume 54 (see FIG. 4) which is sealed at each end by the cured potting compound 48. An outlet port 55 communicates with the volume.

Materials from which the microporous fiber membranes 46 can be made to accomplish the separation of cellular components of blood from noncellular components include certain thermoplastic polymers such as polypropylene. These materials can be formed into hollow fibers by known processes such as solution spinning or melt spinning.

For example, a polypropylene hollow fiber can be manufactured which has a wall thickness of approximately 150 microns, an interior diameter of approximately 320 microns, a maximum pore size of approximately 0.55 microns, and an average pore size of approximately 0.30 microns. Such a hollow fiber is commercially available from Enka A.G., the Federal Republic of Germany, and is well-suited for the purposes herein described.

In an alternate embodiment (not shown), the membrane means 22 can take the form of a device having spaced-apart, generally planar membranes made of the same or comparable microporous material. An example of such a device is disclosed in Edelman et al, U.S. Pat. No. 4,313,813.

The second branch means 42 can be operative for transferring the platelet-rich plasma directly from the centrifugation container 26 to the microporous membrane means 22 (see, e.g., the system 12 in FIG. 3). However, in the FIG. 2 embodiment, the second branch means 42 includes means 56 for temporarily collecting or pooling the platelet-rich plasma prior to filtration. The pooling means 56 includes a pooling container 58 and first transfer conduit means 60 which communicates, at one end, with an outlet port 62 which communicates with the zone in the centrifugation container 26 and, at the other end, with an inlet port 64 in the pooling container 58.

The pooling means 56 further includes valve means 66, such as a manual roller clamp or hemostat, inline with the first transfer conduit means 60 to control the transfer of the platelet-rich plasma. This transfer can be accomplished, after centrifugation, by manually expressing the platelet-rich plasma from the container 26. A pump (not shown) may be used for the same purpose.

The pooling means 56 also includes, in this arrangement, second transfer conduit means 68 which communicates, at one end, with the inlet port 51 of the membrane means 22 and, at the other end, with an outlet port 70 in the pooling container 58. By operatively connecting the portion 43, which in the illustrated embodiment is situated along the second transfer conduit means 68, with the external pump means 24, the platelet-rich plasma can be introduced into the membrane means 22 for filtration.

Valve means 72, again such as a roller clamp or hemostat, is provided inline with the second transfer conduit means 68 for controlling this transfer.

The pump means 24 may be variously constructed. However, in order to meet all of the collection objectives of the system 10, operative contact between the conduit portion 43 and the pump means 24 must not compromise the sterile integrity of, or otherwise "open", the system, as judged by appliable standards in the United States.

In the illustrated embodiment, the pump means 24 takes the form of a conventional peristaltic pump, such as one manufactured and sold by Renal Systems under the trade name MINIPUMP. The pump serves to repeatedly compress and expand the tubing portion and cause whole blood to flow into the hollow fiber membranes 46.

By controlling the pump speed, the proper flow characteristics within the hollow fiber membranes 46 can be maintained to cause effective separation of the cellular components (i.e., the platelets) from the noncellular component (i.e., the plasma).

Plasma which is virtually free of platelets collects in the open volume 54. Meanwhile, platelets, in concentrated form, exit the outlet port 53.

Because the separation of virtually all of the platelets from the platelet-rich plasma occurs essentially simultaneously as the platelet-rich plasma traverses the membrane means 22, significant economies of time can be realized using the system 10. Furthermore, because the system 10 requires only a peristaltic pump or the like to perform the second separation step, economies of labor can also be achieved.

Just as significantly, because the plasma which collects in the volume 54 is virtually platelet-free, the number of platelets present in the concentrate which exits the port 53 is maximized by the system 10 to the greatest extent possible.

The second means 16 also preferably includes a first transfer container 74 or containers (shown in phantom lines) and associated third branch means 76 which transfers the virtually platelet-free plasma from the volume 54 into the first transfer container 74 for storage, or for further fractionation into Factor VIII-rich cryoprecipitate.

The second means 16 also preferably includes a second transfer container 78 or containers (shown in phantom lines) and associated fourth branch means 80 for transferring the platelet concentrate from the outlet port 53 into the second transfer container 78 for storage.

The system 10 also preferably includes a source 82 of sterile saline solution and branch conduit means 84 which communicate with the second means 16 upstream of the microporous membrane means 22. The saline is used to prime the membrane means 22 and purge air from the second means 16 prior to collection. Vent conduit means 85 is preferably provided to circulate the priming volume of saline back to the saline source 82.

Additional valve means 86a, b, c, d, and e are provided inline with, respectively, the first, third and fourth branch means 28, 76, and 80, as well as the priming branch conduit means and vent conduit means 84 and 85, to direct the flow of fluids through the system 10 to carry out the method shown in FIG. 1. The valve means 86a through e may take the form of manually actuated roller clamps or hemostats.

To further enhance the storage of the components which are collected by the system 16, the centrifugation container 26 (in which the red blood cells are collected), the first transfer container 74 (in which the virtually platelet-free plasma is collected ), and the second transfer container 78 (in which the platelet concentrate is collected) are each purposely imparted with a predetermined physical characteristic which is beneficial to the intended storage function of the container. This aspect of the invention will be described in greater detail later herein.

In the embodiment shown in FIG. 2, the first, second, third, and fourth branch conduit means 28, 42, 76, and 80, as well as the priming branch conduit means 85 and vent conduit means 84 and 85, each takes the form of a length of flexible tubing or conduit made of a plastic hemocompatible material, such as plasticized polyvinyl chloride.

Preferably, each length of tubing or conduit offers a fluid path which is closed from communication with the atmosphere, and the system 10 is not thereafter "entered" in a non-sterile fashion as the blood collection procedure takes place. The system 10, once sterilized, thus constitutes a sterile, "closed" system, as judged by applicable standards in the United States. The collected components can thus be stored for the maximum permissible time.

However, it should be appreciated that all or part of the system 10 could be "open" to communication with the atmosphere, or the system 10 could be otherwise "entered" in a non-sterile fashion during the course of the procedure, and still collect components in basically the same fashion. However, the red blood cells and platelet concentrate collected in the "open" system would have to be reinfused within twenty-four hours of collection. Similarly, the virtually platelet-free plasma collected could be used only for fractionation purposes (which includes a subsequent sterilization step).

The system 10 shown in FIG. 2 can be manufactured and sold in various configurations. An illustrative assembly 88 is shown in FIG. 6.

In FIG. 6, the assembly 88 is initially configured into seven separate subassemblies (designated 88a through g). The subassemblies 88a through g can be coupled together by the operator to form the system 10 shown in FIG. 2.

In this arrangement, each subassembly 88a through g is preferably housed in a tear-away protective overwrap 90 in which each subassembly is sterilized. The overwraps 90 are removed at time of use. The overwrap 90 also preferably prevents evaporation of fluids present in any of the subassemblies prior to use (such as saline in the subassembly 88f).

In this arrangement, the assembly 88 further includes means 92 for selectively establishing fluid paths among the normally separate subassemblies 88a through g in a manner which does not compromise the sterile closed integrity of the subassemblies or of the formed system 10 as a whole.

More particularly, the means 92 includes one or more connector means 94 associated with each subassembly. The connector means 94 is carried within the confines of the tear-away overwrap 90 prior to use.

As can best be seen in FIGS. 8 through 11, each connector means 94 includes means 96 for selectively mechanically coupling pairs of the connector means together with a portion 98 of each in facing contact. The facing portions 98 include means 100 operative for melting to form a fluid path through the joined pairs of the connector means 94, thereby opening fluid communication between the various subassemblies, but only in response to exposure to an energy source efficient in itself to effectively sterilize the means 100 as they melt. This constitutes an active sterilization step which occurs simultaneously with the formation of the fluid path.

Furthermore, during the act of melting, the means 100 are preferably operative for fusing together to form a hermetic seal about the periphery of the fluid path. The resulting connection is thus internally sterile and closed from communication with the atmosphere.

The connector means 94 may be variously constructed and employ different means of operation. However, to meet the desired increased-yield objectives of the system 10, the connector means 94 each must meet certain operative requirements.

More particularly, each connector means 94 must (1) normally close the associated subassembly from communication with the atmosphere; (2) be opened only in conjunction with an active sterilization step which serves to sterilize the regions adjacent to the fluid path as the fluid path is formed; and (3) be capable of hermetically sealing the fluid path at the time it is formed.

It has been determined that the sterile connector generally described in Granzow et al U.S. Pat. Nos. 4,157,723 and 4,265,280 meets all of the above criteria and, for this reason, such a connector is shown in the illustrated embodiment.

The construction and operation of such a connector can be best seen in FIGS. 9 through 11, where the connector means 94 used to join the subassembly 88e with the subassembly 88c are shown. It should be appreciated that all of the connector means 94 associated with the other subassemblies operate in the identical fashion.

More particularly, each connector means 94 includes a housing 102 which defines a hollow interior 104 which communicates with its associated subassembly. The heretofore described meltable means 100 takes the form of a meltable wall which normally seals or closes the associated interior, and thus subassembly, from communication with the atmosphere.

The housing further includes a tubular conduit portion 106 which communicates with the interior 104 and which serves to interconnect the connector means 94 to the length of tubing which forms a part of the associated subassembly.

While the connector means 94 may be variously attached to the end of the tubing, in the illustrated embodiment, a hermetic, friction fit between the tubular conduit portion 106 is envisioned. An elastic band 108, such as made from a latex material, preferably encircles the outer periphery of the junction to assure a fluid tight, hermetic fit between the tubular portion 106 and the respective tubing.

To normally prevent fluid flow communication with the interior of the connector means 92 in this arrangement, an inline valve member 110 (shown in phantom lines in FIG. 8) may be provided. Such an arrangement is particularly desirable in association with any fluid-filled container.

While the valve member 110 may be variously constructed, in the illustrated embodiment, it takes the form of an inline frangible valve member, such as one disclosed in Bayham et al, U.S. Pat. Nos. 4,181,140 and 4,294,247.

Alternately, the frangible valve member 110 can form an integral part of the connector housing 102, as is shown in Granzow et al, U.S. Pat. No. 4,265,280.

In the illustrated embodiment, the meltable wall 100 is fabricated from a radiant energy absorbing material. It is thus operative for melting in response to exposure to a source of radiant energy. Furthermore, the material from which the wall 100 is constructed may be purposefully preselected so that it melts only at temperatures which result in the rapid destruction of any bacterial contaminant on the surface of the material (i.e., over 200° C.). To permit the transmission of radiant energy through the housing 102 to the meltable wall 100, the housing 102 is made of a material which minimizes absorption of the particular type of radiant energy selected.

In the preferred embodiment, the wall 100 is made of a material fabricated from poly(4-methyl-1-pentene), which is sold under the trademark TPX by Mitsui Chemical Company. This material has a crystalline melting point of approximately 235° C., and is further discussed in Boggs et al U.S. Pat. No. 4,325,417. The material of the wall 100 is colored black so as to absorb infrared radiation. The housing 102 is made of a clear TPX material which is generally transparent to the passage of radiation.

As can be best seen in FIG. 8, the connecting means 96 takes the form of mating bayonet-type coupling mechanisms, which serve to interlock a pair of connector means 94 together with their radiant energy absorbing walls 100 in facing contact (see FIG. 10). When exposed to a radiant energy source which, in the illustrated embodiment, consists of an incandescent quartz lamp 112 focused on the opaque wall 100, the radiant energy absorbing walls 100 melt and fuse together, as can be seen in FIG. 11. In the process of melting, the walls 100 form a hermetically sealed opening 114 which establishes through the connector means 94 a fluid path which is at once sterile and closed to communication with the atmosphere.

As the following Example 1 demonstrates, the utilization of the illustrated connector means 94 assures a probability of non-sterility which exceeds $10^{-6}$.

EXAMPLE 1

A methanol suspension of $1.5 \times 10^8$ *Bacillus subtilis* var *niger* (globiguii) spores per milliliter was prepared. This organism was chosen because of its high resistance to dry heat (see Angelotti, et al, "Influence of Spore Masture Content on the Dry Heat Resistance of *Bacillus subtilis* var *niger*", Appl. Microbiol., v 16 (5): 735–745, 1968).

Eighty (80) uncoupled sterilized connector members (i.e., forty (40) pairs) identical to the connector means 94 shown in FIGS. 8 through 11, were inoculated with 0.01 milliliter of the *B subtilis* var *niger* (globiguii) suspension. This constituted exposure of the associated walls 100 of each connector member to approximately one million (i.e., $10^6$) spores of the organisms.

Forty (40) of the inoculated uncoupled connectors were each attached to empty, sterile containers. The other forty (40) were each attached to containers containing a sterile microbiological growth medium (soybean casien digest (SCD) broth). These inoculated pairs of connector members will hereafter be referred to as the Test Connectors.

Sixteen (16) additional uncoupled and sterilized connector members (i.e., eight (8) pairs) were inoculated only with methanol. Eight (8) of the connectors were each attached to empty, sterile containers, and eight (8) were each attached to sterile containers containing the SCD broth. These will hereafter be referred to as Negative Control Connectors.

The Test Connectors were coupled together, forming forty (40) connections between the empty containers and the SCD broth containers. The noninoculated Negative Control Connectors were also coupled together, forming eight (8) connections between the empty containers and the SCD broth containers. Each connection was placed within the light-induced melting apparatus as heretofore described to fuse the membranes together and open a fluid path. The medium was then passed through the connections.

Eight (8) additional and already fused connector members were inoculated as Positive Controls. Two of these connections were inoculated with a theoretical challenge of $10^6$ *B subtilis* var *niger* (globigii) spores per connection; two were inoculated with a theoretical challenge of $10^4$ spores per connection; two were inoculated with a theoretical challenge of $10^2$ spores per connection; and two were inoculated with a theoretical challenge of $10^1$ spores per connection. Medium was then flushed through the fluid path of these Positive Control Connectors.

All units were incubated at approximately 32° to 37° C. for up to seven days. After incubation, all turbid broths were subcultured to SCD agar and incubated for 18 to 24 hours at approximately 32° to 37° C. The subcultures were examined for the presence of orange colonies, which is characteristic of the indicator organism.

Upon examination of the forty (40) Test Connections, no turbid broths were observed.

All eight (8) Negative Controls also remained negative during incubation.

All eight (8) Positive Controls demonstrated growth of the indicator organism at all inoculum levels.

Referring again to the assembly 88 shown in FIG. 6, it should be appreciated that two or more of the various subassemblies 88a through g could be integrally joined together during manufacture, thereby reducing the overall number of subassemblies to be joined by the operator.

For example, in an alternate arrangement, the subassemblies 88a and 88b (comprising the centrifugation container 26 and pooling container 58) could constitute an integrally joined unit 89. The unit 89 could be placed in the centrifugation chamber 20.

In this alternate arrangement, the subassemblies 88c, d, and e (comprising the first and second transfer containers 74 and 78 and the microporous membrane means 22) could also be another integrally joined unit 91 separate from the unit 89. The unit 91 would remain outside of the centrifugal chamber during centrifugation, and would be joined to the unit 89 (using a pair of the connector means 94) after centrifugation has taken place.

After the various components have been collected in the in the containers 26, 74, and 78, each container is preferably sealed closed and separated from the system 10. This can be accomplished utilizing conventional means, such as a spaced-apart pair of hand seal clips (not shown), or by the formation of a hermetic, snap-apart seal using a HEMATRON ® dielectric sealer (also not shown) sold by Fenwal Laboratories.

As before explained, in a preferred embodiment, at least a portion of each of the component collection containers 26, 74, and 78 is purposely imparted with a predetermined physical characteristic which is beneficial to the intended storage function of the particular container.

For example, to maximize the storage times of the virtually platelet-free plasma, the transfer container 74 is preferably made of a material having a relatively high low-temperature strength to withstand freezing of the platelet-free plasma for prolonged storage.

Candidate materials for this purpose includes various polyolefin materials, such as low density polyethylene and copolymers of polyethylene and polypropylene, including those containing a major amount of polypropylene.

To maximize the allowable storage time of the platelet concentrate collected in the system 10, the transfer container 78 in which platelet concentrate will be stored preferably has a gas transfer characteristic beneficial to prolonged platelet storage. More particularly, the transfer container 78 would preferably have a gas transfer characteristic which exceeds that of polyvinyl chloride plasticized with di-2-ethylhexylphthalate (DEHP).

For example, the transfer container 78 can include a polyolefin-type container which is disclosed in Gajewski et al, U.S. Pat. No. 4,140,162, or a polyvinyl chloride container which has been plasticized with tri-2-ethylhexyl trimellitate (TEHTM), as disclosed in Warner et al, U.S. Pat. No. 4,280,497.

Alternately, or in addition, the platelet transfer container 78 can include a platelet storage media (not shown) which is suited for maintaining platelet viability during storage.

To enhance the storage of the red blood cells, the centrifugation container 26 is preferably made of a material which is known to suppress hemolysis in red cells during storage. Candidate materials for this purpose include polyvinyl chloride plasticized with di-2-ethylhexylphthalate (DEHP).

Alternately, or in addition, an additional transfer container 116 (shown in FIG. 6 as a part of the subassembly 88g) can be attached to the centrifugation container 26 utilizing the connector means 94. This transfer container 116 includes an isotonic red cell storage solution (designated "S" in FIG. 6) which is suited for suppressing hemolysis during storage. This solution S would be introduced into the red blood cells remaining in the container 26 after the platelet-rich plasma has been removed.

The solution S could include ingredients such as saline, adenine, mannitol, and glucose, such as the solution disclosed in Grode et al, U.S. Pat. No. 4,267,269, or in copending Grode et al, U.S. Pat. application No. 377,110, filed May 11, 1982, and entitled RED CELL STORAGE SOLUTION AND METHOD.

Because red cells are collected utilizing the system 10 (and associated assembly 88), the system 10 can be used to collect and process whole blood from a individual donor once every eight weeks in the United States.

Attention is now directed to the blood component collection system 12 shown in FIG. 3. The system 12 shares many common elements with the system 10 shown in FIG. 2. Common reference numerals are provided for these common elements.

Like the system 10 in FIG. 2, the system 12 includes the first means 14, or portion, for collecting whole blood for separation into essentially red blood cells and platelet-rich plasma. In the system 12, however, pump means 117 is utilized to deliver blood into the centrifugation container 26.

Also like the system 10, the system 12 includes the second means 16, or portion, for receiving the platelet-rich plasma from the first means and for noncentrifugally separating the platelet-rich plasma into platelet concentrate and virtually platelet-free plasma.

Like the system 10, the second means 16 of the system 12 includes the microporous membrane means 22 for filtering the cellular component of blood from the non-cellular components.

However, unlike the system 10 shown in FIG. 2, the first means 14 of the system 12 is operative for use with an extracorporeal blood processing device 19 which is capable of processing blood in a continuous flow procedure. An example of such a device is found in Cullis et al, U.S. Pat. Nos. 4,146,172 and 4,185,629.

Examples of commercially available devices are the CS-3000 ® Blood Cell Separator and the CELLTRIFUGE II ® Blood Cell Seperator, both of which are manufactured and sold by Fenwal Laboratories.

To accommodate the continuous flow procedure, the first means 14 of the system 12 includes fifth branch means 118 which communicates with the centrifugation container 26 for returning the red blood cells to the donor. Valve means 120 is provided inline with the fifth branch means 118 to control the return.

The fifth branch means 118, like all of the heretofore described branch means, preferably takes the form of a length of flexible tubing or conduit made from a hemocompatible material. The fifth branch means 118 includes, at its terminus, another phlebotomy needle 122.

While individual phlebotomy needles 32 and 122 are shown in FIG. 3, it should be appreciated that the first and fifth branch means 28 and 118 could each communicate in common with one double lumen needle of conventional construction (not shown).

The system 12 shown in FIG. 3 optionally includes a third transfer container 124 and sixth branch means 126 for diverting a volume of the red blood cells traversing the fifth branch means 118 away from the donor and into the third transfer container 124 for storage. Valve means 128 is provided inline with the sixth branch means 126 for controlling the transfer of red blood cells into the container 124.

The system 12 shown in FIG. 3 also includes, in addition to the source 82 of sterile saline and associated branch conduit means 84 and 85, a source 130 of sterile anticoagulant solution and branch conduit means 132 for introducing the anticoagulant solution into the system. Valve means 134 is provided inline with the branch conduit means 132 for controlling the introduction of anticoagulant.

Pump means 136, preferably in the form of a peristaltic pump, can be included to meter the introduction of anticoagulant through the branch means 132.

As in the FIG. 2 system 10, the system 12 is preferably closed to communication with the atmosphere throughout the procedure, thereby maximizing the allowable storage times.

To maintain the closed integrity of the system 12 during the continuous flow procedure, the first, second, and fifth branch conduit means 28, 42, and 118, which all communicate with the centrifugation container 26, are consolidated in an umbilicus 138. According to the principles discussed in Adams, U.S. Pat. No. RE 29,738, this umbilicus 138 is preferably rotated during centrifugation at a speed one-half the speed of the container 26.

Twisting of the umbilicus 138 is thereby avoided, and fluid communication through the umbilicus 138 is continuously maintained without the use of rotating seals.

It should be appreciated that the system 12 can be readily adapted for use with a device employing a rotating seal arrangement or the like. However, such an arrangement might compromise the closed sterile integrity of the system 12 as measured by applicable standards in the United States and therefore lead to significantly shortened storage times.

Also unlike the system 10 shown in FIG. 2, the second branch means 42 of the system 12 does not utilize the pooling means 56, but rather transfers the platelet-rich plasma continuously from the container 26 to the microporous membrane means 22 in response to operating the pump means 24.

Figure 7:
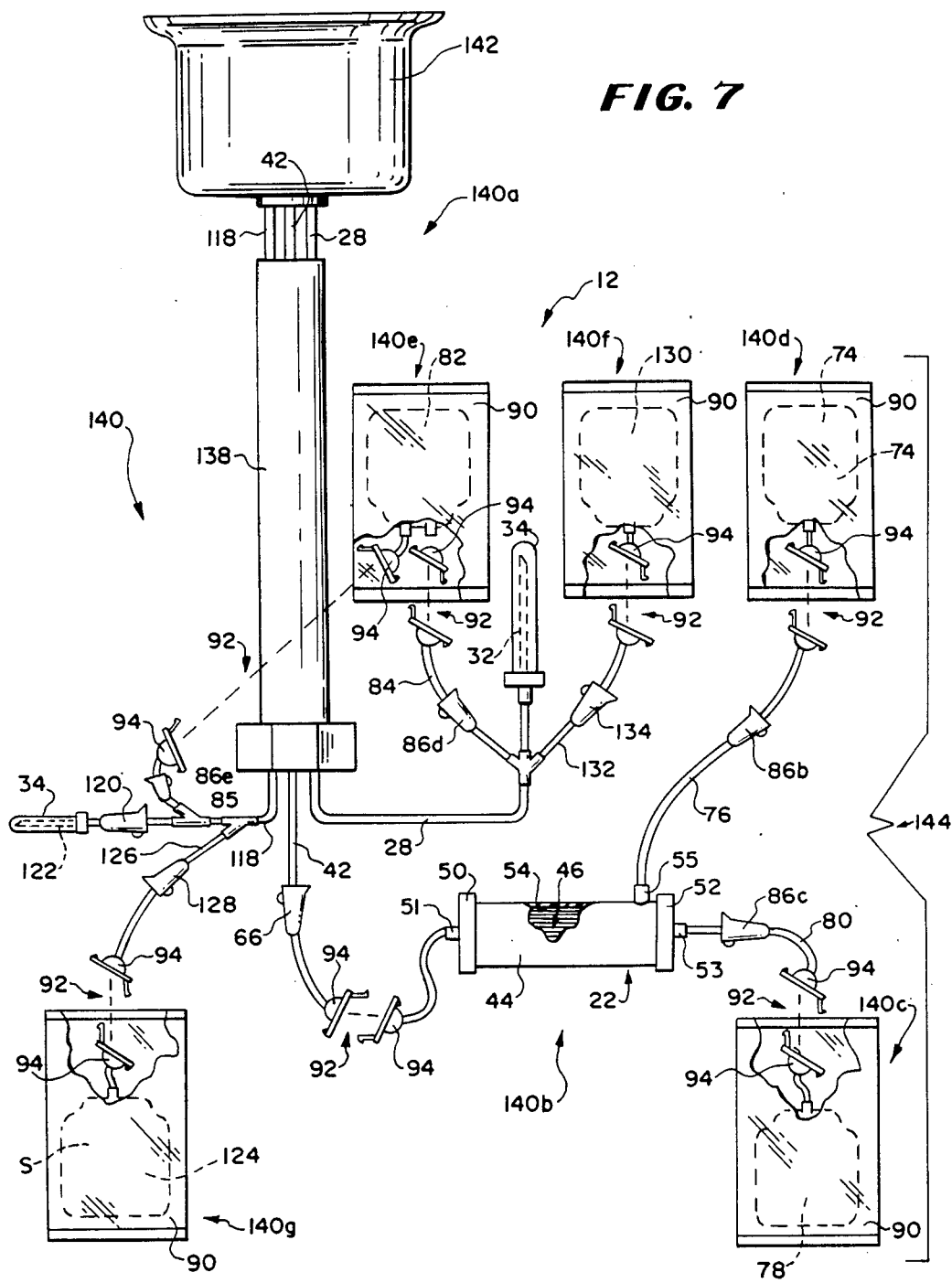
FIG. 7 is a plan view of an increased yield blood component collection assembly which embodies the features of the system shown in FIG. 3.

The system 12 shown in FIG. 3 can be variously constructed. In FIG. 7, a representative assembly 140 of the system 12 is shown.

Similar to the assembly 88 shown in FIG. 6, the assembly 140 includes two or more separate subassemblies (designated 140a through g) which can be selectively joined together by the operator to form the system 12 utilizing the heretofore described connector means 94.

All or some of the subassemblies 140a through g can be carried in the protective overwrap 90. Other elements common to the system 10 and corresponding assembly 88, as well as to the system 12, are assigned common reference numerals in FIG. 7.

In the FIG. 7 assembly, the centrifugation container 26 takes the form of a disposable bowl 142 which fits in the centrifugation chamber of the CELLTRIFUGE II ® Blood Cell Separator. Specific details of the construction and operation of the bowl 142 are disclosed in copending Bachehowski et al, U.S. patent application No. 243,981, filed Mar. 16, 1981 and entitled CENTRIFUGAL PROCESSING APPARATUS AND ROTATABLE PROCESSING BOWL APPARATUS, now U.S. Pat. No. 4,389,206; and Bacehowski et al, U.S. patent application No. 244,398, filed Mar. 16, 1981 and entitled ROTATABLE BOWL ASSEMBLY FOR CENTRIFUGAL PROCESSING APPARATUS HAVING A BONDED AND PREWOUND UMBILICAL SYSTEM, now U.S. Pat. No. 4,389,207. The disclosure of both of these applications is incorporated herein by reference.

As before explained in the context of the assembly 88, two or more of the subassemblies 140a through g could be integrally joined during manufacture to reduce the overall number of subassemblies.

For example, the subassemblies 140b, c, and d (constituting the membrane means 22 and transfer containers 74 and 78) could constitute an integrally joined unit 144.

One or more of the remaining subassemblies 140e, f, and g (constituting the saline and anticoagulant sources 82 and 130 and transfer container 124) could also be integrally joined to the subassembly 140a (constituting the disposable bowl 142 and associated tubing).

Use of the system 12 and associated assembly 140 permits, during a single continuous flow procedure, the collection of the maximum allowable amounts of virtually all of the therapeutic plasma-based components, and (optionally) a unit of red blood cells. Because the system 12 and assembly 140 each comprise, in the preferred embodiments, a closed system as judged by U.S. Standards, all of the collected components are suited for storage for the maximum allowable period.

As before explained, storage of the components can be further enhanced by preselecting the physical characteristics of the containers 74, 78, and 124 to benefit the intended storage function. The red cell storage solution S can also be carried within the third transfer container 124 for intermixing with the collected red blood cells.

If the operator does not collect the optional unit of red cells using the system 12 or assembly 140, the collection procedure can be repeated generally twice a week. If the red blood cells are collected, the procedure can be repeated generally once every eight weeks.

The total volume of components which can be collected in either of the systems 10 or 12 (and each corresponding assemblies 88 and 140) during a given procedure will depend upon the physiology of the donor and maximum allowable total volume permitted by governing regulations.

Nevertheless, either of the systems 10 or 12 is capable of providing optimal yields of platelet concentrate and virtually platelet-free plasma with significant savings in time and labor, when compared to conventional blood collection systems.

EXAMPLE 2

A unit of whole blood (approximately 450 milliliters) was collected from a healthy donor. The unit was subjected to a "soft spin" of 1000 xg for about 6 minutes.

The whole blood was thereby separated into approximately 200 milliliters of red blood cells and approximately 250 milliliters of platelet-rich plasma.

The 250 milliliters of the platelet-rich plasma was next passed through a device such as shown in FIGS. 4 and 5 having approximately 800 polypropylene microporous hollow fibers, each fiber having an effective length of approximately 214 millimeters and a maximum pore size of approximately 0.55 microns. An inlet flow rate of 50 milliliters per minute at an inlet pressure of less than 50 millimeters Hg was maintained for five minutes.

The platelet-rich plasma was thereby separated into approximately 50 milliliters of platelet concentrate containing approximately $6.5 \times 10^{10}$ platelets (which represents a platelet concentration of approximately $1.3 \times 10^6$ platelets per microliter) and 200 milliliters of plasma having a platelet concentration of only about 120 platelets per microliter (thereby constituting virtually platelet-free plasma).

The following Table summarizes the yields and time of the procedure described in Example 2 and compares these to representative yields obtained by conventional nonautomated batch centrifugal processing.

TABLE

| | PLATELET CONCENTRATION IN PLASMA | PLATELET CONCENTRATION IN PLATELET CONCENTRATE | OVERALL ELAPSED TIME |
| --- | --- | --- | --- |
| CONVENTIONAL[1] | Approximately 15,000 Per Microliter (Footnote 2) | Approximately $1.4 \times 10^6$ Per Microliter (Footnote 2) | About 29 minutes (Footnote 3) |
| EXAMPLE | Approximately 120 | Approximately $1.3 \times 10^6$ | 11 minutes |

TABLE-continued

| | PLATELET CONCENTRATION IN PLASMA | PLATELET CONCENTRATION IN PLATELET CONCENTRATE | OVERALL ELAPSED TIME |
| --- | --- | --- | --- |
| 2 | Per Microliter | Per Microliter | |

[1] Based upon Slichter et al, "Preparation and Storage of Platelet Concentrate (Factors Influencing the Harvest of Viable Platelets from Whole Blood)", British Journal of Haematology, 1976, 34, 395–402.
[2] Slichter et al, Ibid, p. 397
[3] Assuming Slichter et al's preferred sequence of a soft spin of 1000 g for 9 minutes and a hard spin of 3000 g for 20 minutes.

Various of the features of the invention are set forth in the following claims.

We claim:

1. A closed blood component collection system comprising
    a first portion suited for use with an extracorporeal centrifugal blood processing device, said first portion including
        a centrifugation container operative for use with the processing device to undergo centrifugation, and
        first branch conduit means connected to said centrifugation container for introducing whole blood from a donor into said centrifugation container for separation therein into red blood cells and platelet-rich plasma in response to centrifugal forces, and
    a second portion operative for attachment to pump means and including microporous membrane means operative for filtering the cellular compoinents of blood from the noncellular components of blood,
    second branch means connecting the centrifugation container with said microporous membrane means and attachable to the pump means for introducing said platelet-rich plasma into said microporous membrane means for filtration int platelet concentrate and virtually platelet-free plasma,
    a first transfer container,
    third branch means communicating with said microporous membrane means and said first transfer container for transferring said virtually platelet-free plasm into said first transfer container,
    a second transfer container,
    fourth branch means communicating with said microporous membrane means and said second transfer container for transferring said platelet concentrate into said second transfer container, and
    each of said branch means in said first and second portions of said system comprising a length of flexible tubing integrally connected with said system to form a fluid path which is closed to communication with the atmosphere.

2. A blood component collection system according to claim 1
    wherein said first portion includes fifth branch means integrally connected with said system and communicating with said centrifugation container and being operative for returning said red blood cells to the donor.

3. A blood component collection system according to claim 2
    wherein said first portion includes
        a third transfer container, and
        sixth branch means integrally connected with said system and communicating with said fifth branch means and said third transfer container for diverting a volume of said red blood cells away from the donor for transfer into said third transfer container.

4. A blood component collection system according to claim 1
    and further including a source of sterile anticoagulant solution and a source of sterile saline solution, and
    wherein said conduit means includes
        seventh branch means integrally connected to said system for introducing the anticoagulant solution into said system, and
        eighth branch means integrally connected to said system for introducing the saline into said system.

* * * * *

UNITED STATES PATENT AND TRADEMARK OFFICE
CERTIFICATE OF CORRECTION

PATENT NO. : 4,680,025
DATED : July 14, 1987
INVENTOR(S) : Robert J. Kruger et al It is certified that error appears in the above-identified patent and that said Letters Patent are hereby corrected as shown below:

Column 19, lines 29-30 - "compoinents" should read -- components --.

Column 19, line 36 - "int" should read -- into --.

Column 19, line 42 - "plasm" should read -- plasma --.

Signed and Sealed this

Twelfth Day of April, 1988

Attest:

DONALD J. QUIGG

*Attesting Officer*   *Commissioner of Patents and Trademarks*